US00PP30991P2

(12) United States Plant Patent
Van Swieten

(10) Patent No.: US PP30,991 P2
(45) Date of Patent: Oct. 29, 2019

(54) ***PHALAENOPSIS* ORCHID PLANT NAMED 'PHALFUEIM'**

(50) Latin Name: ***Phalaenopsis* hybrid**
Varietal Denomination: PHALFUEIM

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 15/932,997

(22) Filed: Jun. 7, 2018

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./311
See application file for complete search history.

(56) References Cited

PUBLICATIONS

UPOV-PLUTO: Plant Variety Database Apr. 11, 2019 citation for 'PHALFUEIM' (1 page).*
EU Community Plant Variety Rights Application No. 2017/1109, Application n°A201701193, filed Apr. 24, 2017, 8 pages.
EU Community Plant Variety Office Official Gazette, Mar. 2017, Jun. 15, 2017, cover page and pp. 37, 57.

* cited by examiner

*Primary Examiner* — Susan McCormick Ewoldt
(74) *Attorney, Agent, or Firm* — Jondle & Associates, P.C.

(57) ABSTRACT

A new and distinct variety of *Phalaenopsis* plant named 'PHALFUEIM', particularly characterized by having small white flowers with light yellow lips, 1 to 4 peduncles that are medium long and sturdy, leaves that are obovate, and is propagated by meristem tissue culture, is disclosed.

3 Drawing Sheets

Genus and species: *Phalaenopsis* hybrid.
Variety denomination: 'PHALFUEIM'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALFUEIM'.

The new *Phalaenopsis* plant is a product of a planned breeding program conducted by the inventor in Bleiswijk, The Netherlands. The objective of this breeding program was to create a new *Phalaenopsis* plant with numerous attractive, small white flowers with light yellow lips, suitable for potted plant production.

The new *Phalaenopsis* plant 'PHALFUEIM' is a result of cross-pollination made by the inventor in February 2008 in Bleiswijk, The Netherlands of the proprietary female, or seed parent, *Phalaenopsis* hybrid '11968-04' (unpatented) with the proprietary male, or pollen parent, *Phalaenopsis* hybrid '01-1810' (unpatented).

The new *Phalaenopsis* was selected by the inventor as a single plant within the progeny of the stated cross-pollination in a controlled greenhouse in Bleiswijk, The Netherlands in February 2011. Asexual reproduction of the new *Phalaenopsis* plant by meristem tissue culture since 2013 in Bleiswijk, The Netherlands, has demonstrated that the new variety reproduces true to type with all of the characteristics, as herein described, firmly fixed and retained through successive generations.

Plant Breeder's Rights for this variety have been applied for in Europe on Apr. 24, 2017. 'PHALFUEIM' has not been made publicly available or sold anywhere in the world more than one year prior to the effective filing date of this application.

SUMMARY OF THE INVENTION

The following are the most outstanding and distinguishing characteristics of this new cultivar when grown under normal horticultural practices in Bleiswijk, The Netherlands and can be used to distinguish 'PHALFUEIM' as a new and distinct variety of *Phalaenopsis* plant.

1) Small white flowers with light yellow lips;
2) 1 to 4 peduncles;
3) Peduncle is medium long and sturdy; and
4) Shape of the leaf is obovate.

DESCRIPTION OF THE PHOTOGRAPHS

This new *Phalaenopsis* plant is illustrated by the accompanying photographs which show the overall plant habit including blooms, buds and foliage of the plant; the colors shown are as true as can be reasonably obtained by conventional photographic procedures. The photographs were taken in a greenhouse in Bleiswijk, The Netherlands, from 50-week old plants in March 2018. Colors in the photographs may differ from the color values cited in the detailed botanical description, which accurately describe the actual colors of the new variety.

DESCRIPTION OF THE NEW VARIETY

Figure 1:
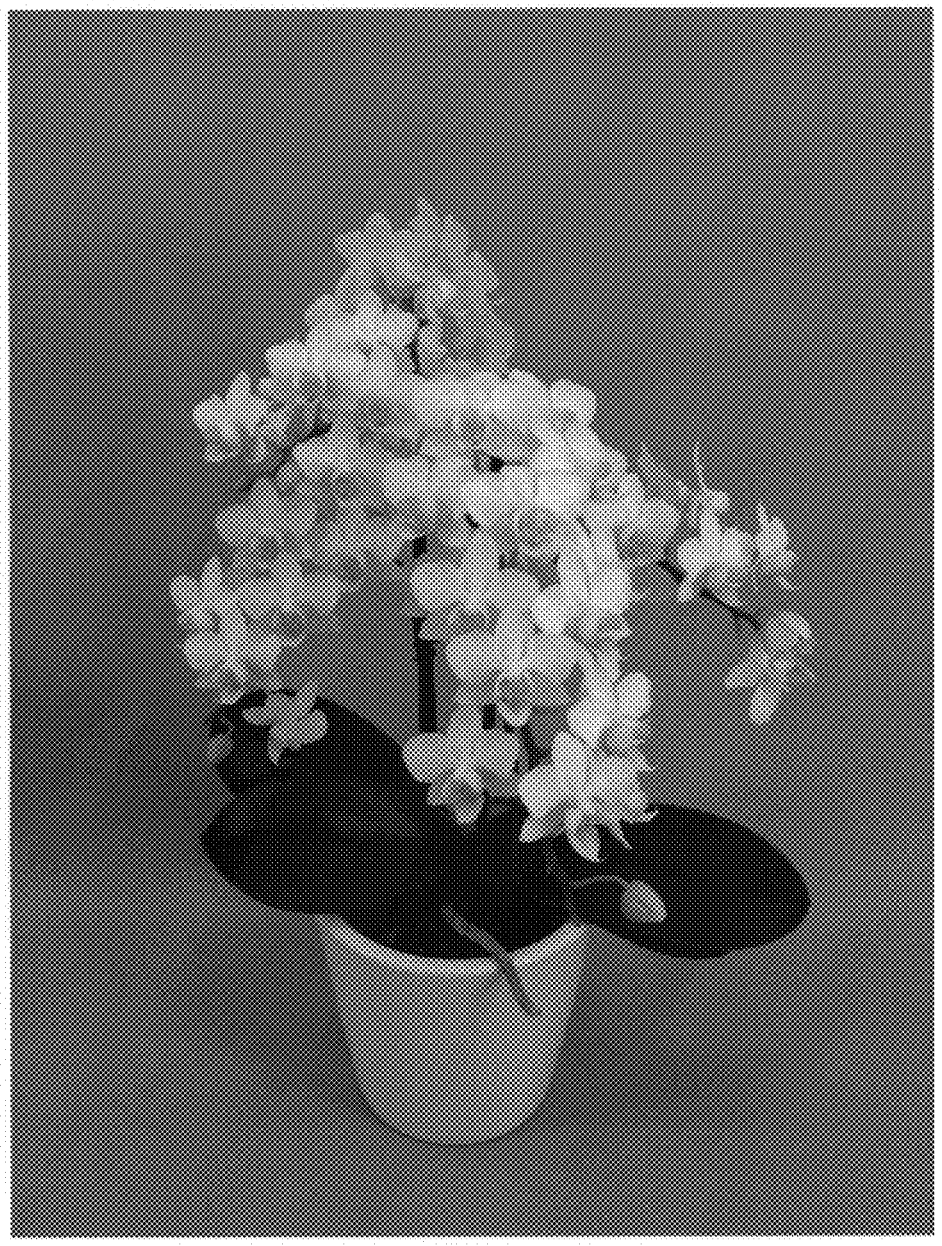
FIG. 1 shows the overall plant habit, including blooms, buds and foliage of 'PHALFUEIM'.
Figure 2:
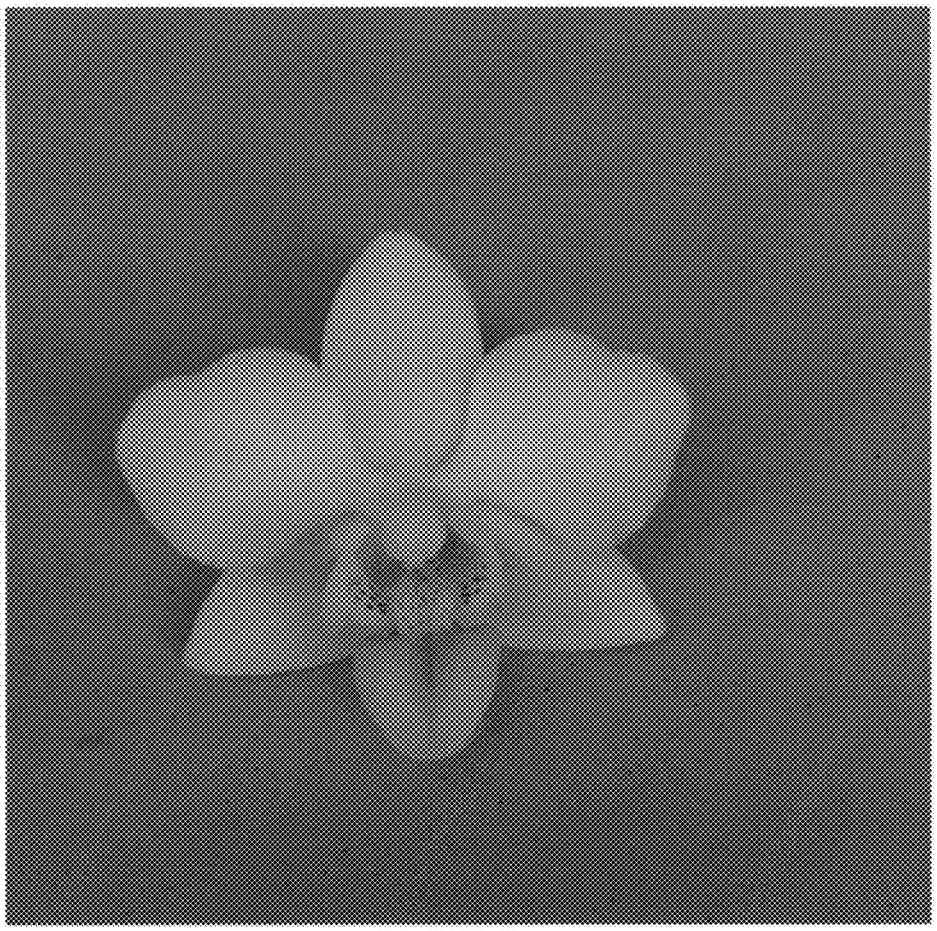
FIG. 2 shows a close-up of a flower of 'PHALFUEIM'.
Figure 3:
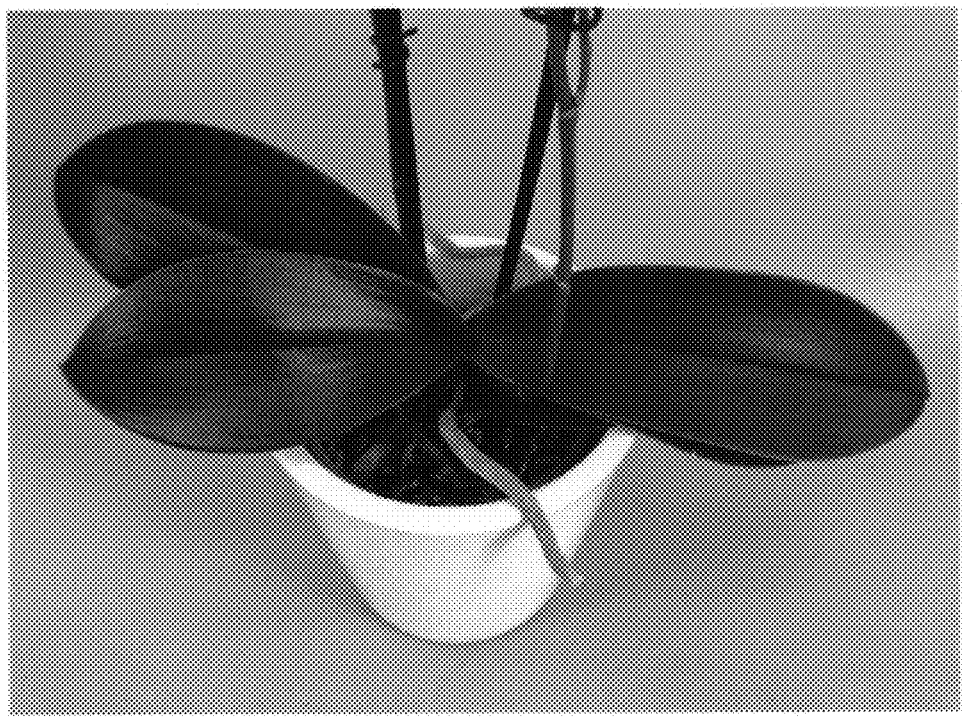
FIG. 3 shows an overhead view of the leaves of 'PHALFUEIM'.

The following detailed description sets forth the distinctive characteristics of 'PHALFUEIM'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, The Netherlands. Observations and measurements were made in March 2018 on flowering plants which were planted in 12 centimeter (diameter) pots. After in-vitro propagation, the plants were grown in nursery trays for 20-24 weeks, followed by transplantation to 12 centimeter (diameter) pots and grown in a greenhouse between 27° C. to 29° C. for 30 weeks, continued by a cooling period of 8 weeks between 18° C. to 20° C. and 12 weeks in a greenhouse of 21° C. Flowering occurs after 50-weeks in a 12 centimeter pot.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALFUEIM'.

Parentage:

*Female parent*.—*Phalaenopsis* cultivar '11968-04' (unpatented).

*Male parent*.—*Phalaenopsis* cultivar '01-1810' (unpatented).

Propagation:

*Type*.—Meristem tissue culture.

Roots:

*Root description*.—Greyed-green colored roots (between RHS 190B and 190C) with branching lateral roots having green (RHS 146D) colored root tips.

Plant:

*Commercial crop time to flowering*.—Following asexual propagation (in-vitro), the rooted cuttings grow for 20-24 weeks. After transplantation in 12 cm pots, the plants are finished after 48 to 50 weeks.

*Growth habit of peduncle*.—Standard, green leaves, raceme to panicle.

*Height* (*from soil level to top of inflorescence*).—Approximately 37.0 cm to 42.0 cm.

*Width* (*measured from leaf tips*).—About 29.0 cm to 31.0 cm.

*Vigor*.—Strong.

Leaves:

*Mature leaves*.—Quantity per plant: 6 to 8 leaves are produced before flowering. Length (fully expanded): 14.5 cm to 16.5 cm. Width: 6.0 cm to 7.0 cm. Shape: Obovate. Base shape: Moderately elongated. Apex: Obtuse unequal. Leaf blade angle with the petiole (measured from the horizontal position): Between 15 degrees and 30 degrees. Leaf margin: Entire. Color: Upper surface: RHS 147A with lighter green margin (RHS 146C). Lower surface: RHS 147B with lighter green margin (RHS 146D). Texture (both upper and lower surfaces): Rough. Thickness: 2.2 mm to 2.5 mm. Venation: Pattern: Parallel. Color of the midvein: Upper surface: RHS 147A. Lower surface: RHS 147B.

Peduncle:

*Quantity per plant*.—1 to 4.

*Number of flowers per peduncle*.—25 to 35.

*Length*.—37.0 cm to 42.0 cm.

*Diameter*.—3.8 mm to 4.1 mm.

*Strength*.—Strong.

*Aspect*.—Upright to slightly pendant.

*Texture*.—Smooth.

*Color*.—Green (RHS 146B).

*Internode length*.—4.0 cm to 5.0 cm.

*Callosities*.—None.

Inflorescence description:

*Appearance*.—Upright to slightly pendant, raceme to panicle inflorescence with bilaterally symmetrical flowers that open in succession beginning with the lowermost flower

*Inflorescence size*.—Height (from base to tip): 200.0 mm to 250.0 mm.

*Flowering time*.—First flowers can be expected 10 to 11 months after planting in a 12 cm (diameter) pot.

*Flower*.—Height: 39.0 mm to 41.0 mm. Diameter: 45.0 mm to 47.0 mm. Depth of lip: 13.0 mm to 16.0 mm.

*Flower longevity*.—On the plant: 8 to 12 weeks.

*Fragrance*.—Absent.

*Flower bud*.—Average size: Small. Length: 14.0 mm to 16.0 mm. Width: 12.0 mm to 14.0 mm. Shape: Egg shaped. Color: Light green (between RHS 145B and 145C).

*Petals*.—Arrangement: Open/free. Shape: Semi-circular. Apex: Rounded asymmetric. Margin: Undulated. Length (from base to tip): 20.0 mm to 22.0 mm. Width: 18.0 mm to 20.0 mm. Color (when fully opened): Upper surface: Basic color: White (RHS NN155C). Over color: Absent. Lower surface: Basic color: White (RHS NN155C). Over color: Absent.

*Dorsal sepal*.—Shape: Elliptic. Apex: Slightly emarginated. Margin: Entire. Length (from base to tip): 20.0 mm to 22.0 mm. Width: 12.0 mm to 14.0 mm. Color (when fully opened): Upper surface: Basic color: White (RHS NN155C). Over color: Absent. Lower surface: Basic color: White (RHS NN155C). Over color: Absent.

*Lateral sepals*.—Shape: Ovate. Apex: Obtuse asymmetric. Margin: Entire. Length (from base to tip): 20.0 mm to 22.0 mm. Width: 13.0 mm to 15.0 mm. Color (when fully opened): Upper surface: Basic color: White (RHS NN155C). Over color: Light green (RHS 145C/D) and very small dots (RHS 71A) at the base. Lower surface: Basic color: White (RHS NN155C). Over color: Light green (between RHS 145C and 145D) at the base.

*Labellum* (*lip*).—Whiskers: Present. Length of whiskers: 1.0 mm to 3.0 mm. Color of whiskers: White (RHS NN155C). Pubescence on the lip: Absent.

*Lateral lobe*.—Shape: Type IV (as described in the International Union for the Protection of New Varieties of Plants (UPOV) Test Guidelines for *Phalaenopsis*); weakly spatulate. Margin: Entire. Length:

12.0 mm to 14.0 mm. Width: 7.0 mm to 9.0 mm. Color: Upper surface: White (RHS NN155C); red-purple dots (RHS 71A) at the base and yellow region (RHS 7A) toward one margin. Lower surface: White (RHS NN155C) with a yellow (RHS 6A) edge at the front.

*Apical lobe*.—Shape: Ovate. Margin: Entire. Length: 10.0 mm to 12.0 mm. Width: 11.0 mm to 13.0 mm. Color: Upper surface: Greenish-yellow (RHS 2A) with very small dots (RHS 174A) at the base; white toward the whiskers. Lower surface: White (RHS NN155C) with a yellow (RHS 6A) edge at the back.

*Callus*.—Average size: Small. Height: 4.0 mm to 5.0 mm. Length: 4.0 mm to 5.0 mm. Width: 3.0 mm to 4.0 mm. Color: Yellow (between RHS 9B and 9C) with very small dots (RHS 71A).

Reproductive organs:

*Column*.—Length: 8.0 mm to 10.0 mm. Diameter: 3.6 mm to 3.8 mm. Color: White (RHS NN155C).

*Pollinia*.—Quantity: 2. Diameter: 0.7 mm to 0.9 mm. Color: Orange (RHS 24A).

*Ovary*.—Length: 16.0 mm to 18.0 mm. Diameter: 1.5 mm to 1.8 mm.

*Pedicel*.—Length: 35.0 mm to 38.0 mm. Diameter: 1.9 mm to 2.3 mm. Color: Green (RHS 145A) at the base and light green (between RHS 145C and 145D) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALFUEIM' differs from female parent plant '11968-04' (unpatented) in that 'PHALFUEIM' has ovate, greenish-yellow apical lobes with very small dots at the base, and a light green lateral sepal over color, whereas '11968-04' has triangular apical lobes with light yellow at the base, and lateral sepals with no over color.

'PHALFUEIM' differs from male parent plant '01-1810' (unpatented) in that 'PHALFUEIM' has an even flower pattern, greenish-yellow apical lobes with very small dots at the base and white toward the whiskers, and a light green lateral sepal over color, whereas '01-1810' has a striped flower pattern, apical lobes that are greenish-yellow at the base and purple toward the whiskers, and a light purple lateral sepal over color.

'PHALFUEIM' is most similar to the commercial *Phalaenopsis* plants named 'PHALDUXI' (U.S. Plant Pat. No. 25,680) and 'PHALDRIDOP' (U.S. Plant Pat. No. 28,980). 'PHALFUEIM' differs from the commercial variety 'PHALDUXI' in that 'PHALFUEIM' has a rounded petal apex, an undulated petal margin, and weak curvature of the lateral lobe, whereas 'PHALDUXI' has an obtuse petal apex, an entire petal margin, and medium curvature of the lateral lobe. Additionally, 'PHALFUEIM' has smaller flowers, shorter whiskers and shorter depth of lip than 'PHALDUXI'.

'PHALFUEIM' differs from the commercial variety 'PHALDRIDOP' in that 'PHALFUEIM' has a rounded petal apex, an undulated petal margin, a dotted lateral sepal pattern, and green peduncles, whereas 'PHALDRIDOP' has an obtuse petal apex, an entire petal margin, an even lateral sepal pattern, and peduncles that are a mix of green and light brown. Additionally, 'PHALFUEIM' has smaller flowers, shorter whiskers and shorter depth of lip than 'PHALDRIDOP'.

I claim:

1. A new and distinct variety of *Phalaenopsis* plant named 'PHALFUEIM', substantially as described and illustrated herein.

* * * * *